United States Patent [19]

Goldstein et al.

[11] Patent Number: 4,851,333

[45] Date of Patent: Jul. 25, 1989

[54] **METHOD AND COMPOSITION FOR THE DETECTION AND DIAGNOSIS OF *LEGIONELLA PNEUMOPHILA***

[75] Inventors: Lynn C. Goldstein, Seattle; Larry H. Gosting, Snohomish, both of Wash.

[73] Assignee: Genetic Systems Corporation, Seattle, Wash.

[21] Appl. No.: 583,103

[22] Filed: Feb. 24, 1984

[51] Int. Cl.$^4$ .................. A61K 39/40; C12N 5/00; G01N 33/569; G01N 33/577
[52] U.S. Cl. ........................... 435/7; 435/172.2; 435/188; 435/240.27; 435/948; 436/518; 436/519; 436/526; 436/533; 436/534; 436/548; 436/825; 530/350; 530/387; 530/391; 530/806; 530/808; 530/825; 935/104; 935/110
[58] Field of Search .............. 435/7, 240, 172.2, 188, 435/948; 260/112 R; 424/87; 935/90, 95, 104, 106, 108, 110; 436/526, 548, 811, 825, 518, 533, 534; 240/240.27; 530/354, 387, 391, 806, 808, 825

[56] References Cited

PUBLICATIONS

L. H. Gosting et al, *Journal of Clinical Microbiology,* 20, 1031–1035, 1984.
R. C. Nowinski, *Science,* 219, 637–644, 1983.
R. M. McKinney et al, *Journ. Clin. Microbiol.,* 12, 395–401, 1980.
W. Ehret et al, *Zbl. Bakt. Hyg., I Abt. Orig. A,* 255, 33–38, 1983.
M. F. Para et al, *Journ. Clin. Microbiol.,* 18, 895–900, 1983.
J. R. Joly et al, *Infect & Immunity,* 35, 721–729, 1982.
K. H. Wong et al, *Ann. Int. Med.,* 90, 634–638, 1979.

*Primary Examiner*—Robert J. Warden
*Assistant Examiner*—David A. Saunders
*Attorney, Agent, or Firm*—Townsend and Townsend

[57] ABSTRACT

Method and compositions including monoclonal antibodies to a serogroup-common antigen are provided for the detection and diagnosis of *Legionella pneumophila.* The monoclonal antibodies recognize a proteinaceous antigen of molecular weight 28,000–29,000 Daltons which is detected in at least serogroups 1 through 8 of *Legionella pneumophila* and is not detected in other common respiratory pathogens.

29 Claims, No Drawings

METHOD AND COMPOSITION FOR THE DETECTION AND DIAGNOSIS OF *LEGIONELLA PNEUMOPHILA*

1. Technical Field

This invention relates generally to monoclonal antibodies and more particularly to methods and compositions for the detection and diagnosis of the bacterium *Legionella pneumophila* using monoclonal antibodies to a serogroup-common antigen.

2. Background Art

Legionnaire's disease, first characterized in 1977, is of great clinical interest as an acute human illness with a high mortality. In most patients the infection is manifested as pneumonia, however a second clinical syndrome, Pontiac fever is a non-pneumonic, mild and self-limited respiratory illness.

The most common etiological agent of legionnaire's disease is *Legionella pneumophila,* a gram-negative bacterium which has at least eight recognized serogroups. Laboratory diagnosis of the disease is presently demonstrated by a four-fold increase in serum indirect fluorescent antibody (IFA) titer, together with isolation and culture of Legionella from clinical specimens. Direct fluorescent antibody (DFA) examination of clinical specimens has been carried out with conjugated antisera provided by the Centers for Disease Control, Atlanta, Ga.

The DFA test is the most rapid means of diagnosis of legionnaire's disease in the laboratory, but there are several associated problems. Multiple antibody reagents are required in order to identify all presently recognized serogroups. In addition, cross-reactions with strains of *Pseudomonas fluorescens, Pseudomonas alcaligenes, Bacteroides fragilis* and the Flavobacterium-Xanthomonas group have been reported when conjugates of polyclonal antibodies are used for diagnosis.

The development of monoclonal antibody hybridoma technology (Kohler, G. and C. P. Milstein, Nature 256:495–497 (1975)) gives the field of serology the techniques to produce powerful probes of great specificity and reproducibility. Monoclonal antibodies are generated from the immortalized progeny of a single B-lymphocyte. Each B-lymphocyte produces antibodies specific for a single complementary site on an antigen, called the antigenic determinant. However, such specificity can be detrimental when the objective is to provide an antibody reagent capable of recognizing multiple serogroups of *Legionella pneumophila.*

Serological techniques utilizing polyclonal antisera have been used to identify serogroup common antigens of *Legionella pneumophila.* A positively-charged antigen has been identified in six serogroups of *Legionella pneumophila;* this antigen has not been identified in the closely related species *Legionella micdadei* (Joly, J. R. and G. E. Kenny, Infect. Immun. 35:721–729 (1982)). Other antigens identified in *Legionella pneumophila* serogroup 1 have been shown to occur in as many as five other serogroups (Collins, M. T. et al., Infect. Immun. 39:1441 (1983)). Other studies identifying shared antigens have been conducted by Wong, K. H. et al., Ann. Intern. Med. 90:634–638 (1979), and Hindahl, M. S. and B. H. Iglewski, Abstracts Ann. Meet. Am. Soc. Microbiol., page 329 (1983).

The development of monoclonal antibodies specific for serogroup 1 has been reported in the literature (Sethi et al., J. Clin. Microbiol. 17:953–957 (1983); Para, M. F. and J. F. Plouffe, J. Clin. Microbiol. 18:793 (1983); Joly, J. R. et al., J. Clin. Microbiol. 18:1040 (1983); Guillet et al., J. Clin. Microbiol. 18:793 (1983)). The development of a monoclonal antibody reactive with serogroups 1–6 has been reported, but the nature of the identified antigen was not disclosed (Para and Plouffle, J. Clin. Microbiol. 18:895(1983)).

DISCLOSURE OF THE INVENTION

In one aspect of this invention methods are provided for the detection and diagnosis of the bacterium *Legionella pneumophila,* serogroups 1 through 7, comprising reacting a sample suspected of containing said bacterium with a labeled monoclonal antibody to a serogroup-common antigen and detecting the presence of *Legionella pneumophila* by means of the signal provided by said label. The methods of this invention utilize monoclonal antibodies to a serogroup-common proteinaceous antigen having a molecular weight between 28,000 and 29,000.

In another aspect, this invention provides monoclonal antibodies which identify an antigen common to serogroups 1 through 8 of *Legionella pneumophila* and which do not react substantially with other common respiratory pathogens.

A further aspect of this invention provides an antigenic determinant present on an antigen derived from any of serogroup 1 through 6 of *Legionella pneumophila,* which antigenic determinant is present in at least serogroups 1 through 8 of *Legionella pneumophila,* is not present in *Pseudomonas fluorescens, Legionella bozemanii, Legionella micdadei, legionella dumoffii, Legionella longbeachae* 1 and 2, *Legionella jordanis, Legionella gourmanii, Legionella oakridgensis,* or *Legionella sainthelinsi,* and is found on an antigen having a molecular weight between 28,000 and 29,000, which antigen is proteinaceous.

The hybridoma cell line of the present invention, LP3-IIG2, together with the monoclonal antibodies produced therefrom, was deposited on Jan. 17, 1984 at the American Type Culture Collection, 12301 Parklawn Drive, Rockville, Md. 20852, and was assigned the ATCC Accession Number HB 8472.

BEST MODE FOR PRACTICING THE INVENTION

In accordance with the subject invention, methods, monoclonal antibodies and antigenic determinants are provided for the detection and diagnosis of *Legionella pneumophila.* The serogroup-common antigen has not been identified on a variety of other common respiratory pathogens including *Haemophilus influenzae,* Pseudomonas sp. and Mycoplasma sp.

The antibodies of the present invention are prepared by fusing mammalian lymphocytes, which have been obtained from the spleens of mammals immunized by *Legionella pneumophila* serogroups 1 through 6, with a drug-resistant myeloma cell line in the presence of polyethylene glycol. Fusion hybrids are cultured in hypoxanthine/aminopterin/thymidine (HAT) selective medium and colonies are isolated whose supernatant fluids contain antibody specifically reactive with *Legionella pneumophila.* Monoclonal antibodies can then be prepared in quantity by injecting hybridoma cells intraperitoneally into mice primed with Pristane. Thereafter ascites fluid containing monoclonal antibodies is recovered from the abdominal cavity of the mouse.

The lymphocytes used in the present invention can be derived from the spleen of any host mammal, such as for example rodents. The host can be sensitized by injection of the isolated antigen or alternatively by injection of the entire organism, e.g. *Legionella pneumophila*. The initial immunization is generally followed by a series of booster injections and subsequent isolation of the spleen.

Compositions of the subject invention may be labeled with any known label for use in diagnostic immunoassays or in any procedure which requires precise discrimination of one organism from another. Known labels include fluorescent compounds, enzymes, chemiluminescent compounds, radioisotopes, and particles including, for example, polymerized beads and magnetic particles, among others. For any chosen label, binding of the antigen or antibody provides for the detection and measurement of the complementary composition.

There are numerous immunoassay methods which employ different labels bound to antibodies or antigens. These can be heterogeneous or homogeneous and can include, for example, enzyme-linked immunosorbent assays (ELISA), radioimmunoassays (RIA), and sandwich assays, among others.

These immunoassay methods can include the addition of a surfactant or solubilizing reagent which can, e.g., expose antigenic determinants which are not readily accessible to the labeled compositions. These solubilizing reagents are well known in the art and can include, e.g., Triton ®X-100 (Triton is a registered trademark of Rohm and Haas Co. for octylphenoxypolyethoxyethanol), sodium dodecyl sulfate (SDS), and Nonidet P-40 (NP-40)(Nonidet 40 is a registered trademark of the Shell Company for octylphenoxypolyethoxyethanol), among others. A method for detecting *L. pneumophila* in a biological specimen may comprise contacting a sample of said biological speciment suspected of containing *L. pneumophila with a solubilizing reagent before reacting said sample with a labeled antibody, wherein the label may be a fluorophore.*

The antibodies of the subject invention specifically recognize and bind to an antigen common to at least serogroups 1 through 8 of *Legionella pneumophila* and are not substantially cross reactive with other common respiratory pathogens. The serogroup-common antigen identified by the antibodies of this invention has a molecular weight between 28,000 and 29,000, as determined by electrophoresis in sodium dodecyl sulfate-polyacrylamide gels (SDS-PAGE). It is substantially degraded by proteinase K and is therefore inferred to be proteinaceous. A determinant thereon is recognized by monoclonal antibody LP3-IIG2 (HB 8472).

Having identified the serogroup-common antigen by the criteria of molecular weight, susceptibility to proteinase K and reactivity with LP3-IIG2, it is possible to produce other antibodies which will be reactive with the same antigen and hence cross react with serogroups 1–8 of *Legionella pneumophila.* These antibodies may react with the same antigenic determinant as LP3-IIG2 or they may react with different determinants on the same antigen.

The method of the subject invention is useful for the detection and diagnosis of *Legionella pneumophila.* Briefly, a sample suspected of containing said bacterium is reacted with a labeled monoclonal antibody to a serogroup-common antigen. After washing to remove unbound, labeled antibody, the signal emitted by the label is detected and quantified using appropriate means. The sample is typically of biological origin including such specimens as sputum, lung tissue, blood or urine. The subject methods also can be used to confirm the identity of the organism of interest in culture.

The following examples are provided by way of illustration rather than for limitation.

EXAMPLE

A. Bacterial Strains

The following bacterial strains were obtained from the Centers for Disease Control: *L. pneumophila,* serogroup 1, Philadelphia 1 strain; *L. pneumophila,* serogroup 2, Togus 1 strain; *L. pneumophila,* serogroup 3, Bloomington 2 strain; *L. pneumophila,* serogroup 4, Los Angeles 1 strain; *L. dumoffii; L. Longbeachae* 1; *L. gourmanii;* and *L. sainthelinsi.*

*Legionella pneumophila,* serogroup 5, Dallas 1 E (ATCC 33216); *L. pneumophila,* serogroup 6, Chicago 2 (ATCC 33215); *L. pneumophila,* serogroup 7, Chicago 8 (ATCC 33823); *L. micdadei* (ATCC 33218); *L. bozemanii* (ATCC 33217); *L. Longbeachae* 2 (ATCC 33484); *L. jordanis* (ATCC 33623); and *L. oakridgensis* (ATCC 33761) were obtained from the American Type Culture Collection, Rockville, Md. An isolate of *Pseudomonas fluorescens* was obtained from Harborview Medical Center, Seattle, Wash.

B. Preparation of Immunogens

Legionella microorganisms were grown on charcoal yeast extract agar (Feeley, J.C., et al., J. Clin. Microbiol. 10:437–441 (1979) for two to seven days. Bacterial cells were washed from the surface of the plates with sterile water and then washed three times with water. Alternatively, heavy suspensions of microorganisms were scraped from the charcoal yeast extract agar plates for inoculation into defined medium broth (Reeves, M. W., et al., J. Clin. Microbiol. 13:688–695 (1981)). The cultures were grown for one to three days wtth stirring at 37° C. The cultures were harvested and washed three times with sterile water. The bacteria were fixed in 0.5 percent by volume formalin in physiological saline or were treated with 0.05 mM ethylenediaminetetraacetic acid (EDTA). The suspensions were frozen and stored at −70° C.

C. Mice

BALB/c mice were originally obtained from the Jackson Laboratory (Bar Harbor, Me.) and were bred at the Genetic Systems Corporation, Seattle, Wash. animal facility.

D. Immunizations

Spleen cells for fusions were obtained from BALB/c mice that had been immunized with *L. pneumophila* serogroups 1–6. The immunization schedule consisted of intraperitoneal injections (100 μg protein/0.5 ml) on day 1, followed by 25 μg/0.5 ml injections on days 22, 37, 44, 58, 79, 86, 93, 98, 125 and 142. A final injection of 15 μg was given by intravenous route on day 149. The spleen was removed from an immunized mouse on day 152.

E. Hybridization Procedure

The myeloma cell line BALB/c MOPC 21 NSI/1 (NS/1) was obtained from Dr. C. Milstein (Molecular Research Council, Cambridge, England). This cell line is also available from the ATCC. This variant cell line produces K light chains, but not γ heavy chains; as a consequence, these cells do not secrete immunoglobulins into the culture supernatant. The NS-1 cells are resistant to 8-azaguanine.

NS-1 cells were routinely grown in RPMI 1640 (GIBCO, Grand Island, N.Y.) containing 15 percent heat-inactivated fetal calf serum, 1 mM glutamine and 1 mM pyruvate (RPMI-Hybrid). The spleen cell suspension was prepared by gently dissociating the cell by pressing the organ between the frosted portions of microscope slides with a rotating motion. The slides were frequently dipped into medium to facilitate release of cells. The cell suspension was filtered through a fine nylon screen. The spleen cell suspension was washed three times in serum-free RPMI; the NS-1 cells were washed twice in serum-free RPMI.

Immune spleen cells and NS-1 cells were fused in a 4:1 ratio in 40 percent polyethylene glycol (PEG 1450, Eastman Organics) by centrifugation at 400×g for 5 minutes at room temperature (RT). The cells were washed in 10 ml of RPMI-Hybrid and centrifuged at 160×g for 5 minutes at RT. The supernatant fluid was aspirated and the cells were gently resuspended to $1.5 \times 10^6$ cells/ml in RPMI-Hybrid supplemented with HAT medium (RPMI-Hybrid containing $1.0 \times 10^{-4}$ M hypoxanthine, $4.0 \times 10^{-7}$ M aminopterin, and $1.6 \times 10^{-5}$ M thymidine). This hybrid cell suspension was mixed with feeder thymocytes obtained from 3 to 5 week old BALB/c mice to a final concentration of $1.5 \times 10^6$ thymocytes/ml. The final cell suspension was seeded in 200 µl volumes into the wells of 96-well tissue culture cluster plates (Costar, Cambridge, MA). Additional feedings with HAT medium (50 percent substitution by volume) were given on days 2, 4, 6 and 8. Cultures were routinely incubated at 37° C. in 6 percent $CO_2$. After the cells reached 50 percent confluence (approximately nine days after the fusion), the culture fluids were assayed by enzyme-linked immunosorbent assay (ELISA) for the presence of anti-L. pneumophila antibodies. Hybrid cells that were producing antibodies of the appropriate specificity were then passaged at low density (ten hybrids per well) on a feeder cell layer of thymocytes ($8.0\times10^5$ cells/well).

Culture fluids from the passage 1 wells were assayed by ELISA (described below), and cells that continued to produce anti-*L. pneumophila* antibodies were cloned by limiting dilution (1 cell/well) on thymocyte feeder layers in microtest plates. The wells were scored microscopically five to seven days after seeding to select those wells supporting growth of only one clone. The clones were transferred to a single plate, and their culture fluids were assayed by ELISA after 48 hours growth. Three clones were selected for a second round of cloning in the manner described above.

Clones were expanded in number by daily passage in RPMI-Hybrid. The BALB/c mice used to produce ascites fluid were primed with a 0.5 ml intra-peritoneal injection of Pristane (2, 6, 10, 4-tetramethyl pentadecane; Aldrich Chemical Co., Milwaukee, Wis.) 8 weeks before the inoculation of hybrid cells. Mice were inoculated intraperitoneally with $5\times10^6$ hybrid cells. Ascites fluids from these hybridoma-bearing mice were analyzed for the presence of monoclonal immunoglobulins by serum protein electrophoresis (Beckman Paragon Electrophoresis System; procedure provided by manufacturer). Visual inspection of the stained gel showed the presence of a monoclonal antibody band in the gamma region.

F. ELISA for Detecting Antibody to *L. pneumophila*

Anti-*L. pneumophila* antibodies in culture supernatant fluids and ascites were detected by ELISA on antigen-coated plates. Bacterial suspensions of *L. pneumophila* serotypes 1–6, previously treated with 0.05 mM EDTA, and *Pseudomonas aeruginosa*, Fisher 7 strain (negative control), were diluted in phosphate-buffered saline (PBS), pH7.1 to a final concentration of 45 μg protein/ml. Protein concentrations were estimated by the method of Lowry et al., J. Biol. Chem. 193:265–275 (1951). The plates were coated with antigen by adding 50 μl well of the diluted suspension to 96-well plates (Linbro Tissue Culture Multi-Well Plate; Flow Laboratories, Inc., McLean, VA). The plates were centrifuged at 740×g for 20 minutes at room temperature. The supernatant fluids were removed by aspiration, and 50 μl of 95 percent ethanol was added to each well to fix the antigens to the plate. The plates were left at room temperature for 30 minutes, then they were washed once with PBS, pH 7.1. Fifty μl of 1 percent by weight bovine serum albumin (No. A- 2153, Sigma Chemical Co., St. Louis, Mo.) in PBS was added to each well, and the plates were incubated at room temperature for 1 hour. The wells were washed three times with PBS containing 0.05% (v/v) polyoxyethylenesorbitan monolaurate (Tween®-20; P-1379, Sigma Chemical Co., St. Louis, Mo.). A final wash used deionized water. The final wash water was removed by "flicking" the plates, then the plates were dried in a laminar flow air hood. The plates were sealed nnd stored at 4° C. until use.

Culture supernatant fluids were tested for the presence of anti-*L. pneumophila* antibodies by replica plating (50 μl well) on plates coated with *L. pneumophila* serogroups 1, 2, 3, 4, 5, 6 or *P. aeruginosa.* The plates were incubated at 37° C. for 45 minutes, then the culture fluids were removed and the wells were washed three times with PBS-Tween® 20. Protein A-peroxidase (Cat. No. 10-1023; Zymed Laboratories, Inc., South San Francisco, Ca.) was added to the wells (50 μl well of 1:3,000 dilution of the stock reagent in PBS-Tween® 20). The plates were incubated at room temperature for 30 minutes then washed three times with PBS-Tween® 20. Substrate solution was prepared by dissolving 7 mg of o-phenylenediamine (Cat. No. P-3888; Sigma Chemical Co.) in 50 ml of phosphate-citrate buffer (0.05 M citric acid, 0.1 M sodium phosphate dibasic). Twenty-five μl of 30 percent $H_2O_2$ was added to the substrate solution just prior to use. The substrate solution was added to the wells in 100 μl volumes and the plates were incubated at room temperature in the dark for 30 minutes. The reaction was stopped by adding 50 μl of 3N $H_2SO_4$ to each well and the colorimetic reactions were quantified with a Microelisa Auto Reader (MR580; a trademark of Dynatech Laboratories, Inc., Alexandria, VA).

G. Identification of a Serogroup-Common Antigen

The monoclonal antibodies produced above were analyzed by reaction with *L. pneumophila* antigens that had been electrophoretically separated according to molecular weight and then transferred to nitrocellulose membranes (BA85; Schleicher and Schuell, NH) by electrophoresis (Towbin et al., Proc. Nat. Acad. Sci. USA 76:4350–4354 (1979)). Solubilized antigen preparations of *L. pneumophila* serogroups 1–7, *L. bozemanii* and *L. micdadei* (negative controls) were made by incubating concentrated live cultures of Legionella organisms in a solubilization buffer (Shechter and Black, J. Biol Chem. 246:7690–7696 (1971)) (0.3% sodium deoxycholate, 0.02 M 2-mercaptoethanol, 30% glycerol, 0.03 M. Tris HCl pH 7.6) overnight at 4° C. The suspensions were dialyzed against physiological saline containing 0.3% Bio-beads SM-2 (Bio-Rad Laboratories, Richmond, CA) and subjected to SDS-polyacrylamide gel electrophoresis in 14 percent slab gels. Antigens in the gel were then transferred to nitrocellulose paper by electrophoresis for 2 hours at 27 V in 25 mM sodium phosphate buffer pH7.0 (Bittner et al., Anal. Biochem. 102:459-471 (1980)). After transfer, the nitrocellulose membrane (NCM) was immersed in PBS-Tween ® 20 and incubated at room temperature for 1 hour on a rocking platform. The PBS-Tween ® 20 (Tween is a registered trademark of Atlas Chemical Indust., Inc. for polyoxyethylene (20) sorbitan monolaurate) was poured off and the NCM was cut into strips. Strips were incubated with normal mouse serum (NMS) diluted 1:170 in PBS-Tween ® 20) as a negative control; with immune serum from a mouse immunized as described above (1:170 dilution in PBS-Tween ® 20); or with ascites fluid (1:100 dilution in PBS-Tween ® 20) prepared from a mouse innoculated with hybridoma LP3-IIG2, produced as described above. The NCM strips were incubated in the antibody solutions for 1 hour on a platform rocker. The antibody solutions were then poured off and the NCM strips were washed by four 5 minute incubations with PBS-Tween ® 20 on a platform rocker. After the last wash, the strips were immersed in a solution of protein A-HRP (diluted 1:2,000 in PBS-Tween ® 20) and incubated at room temperature for 1 hour on a platform rocker.

The protein A-HRP solution was poured off and the strips were washed as described above. The strips were immersed in substrate solution (Bio-Rad Laboratories, Richmond, Caif.; procedure available from the manufacturer) for 20 minutes. The reaction was stopped by immersing the NCM strips in deionized water.

The monoclonal antibody, LP3-IIG2 recognized a single antigen present in at least serogroups 1-8 of *L. pneumophila*. This antigen was not detected by LP3-IIG2 in *L. bozemanii* or *L. micdadei*.

The molecular weights of the blotted-antigens were determined by including protein markers (Prestained Protein Molecular Weight Standards for SDS-PAGE, Bethesda Research Laboratories, Inc., Gaithersburg, Md.) in the SDS-PAGE. The relative migrations versus the logarithms of the molecular weights of the standards were evaluated by linear regression to derive molecular weight values for *L. pneumophila* antigens.

The molecular weight of the antigen identified by LP3-IIG2 when blotted from an SDS-PAGE under reducing conditions (4.8% (v/v) 2-mercaptoethanol, in the sample buffer) was 28,000–29,000 for serogroups 1–7.

Solubilized antigen preparations of *L. pneumophila* serogroups 2 and 4, prepared as described above, were diluted to 50 μg protein/ml in carbonate-bicarbonate buffer, pH 9.6 and aliquoted into glass tett tubes. Proteinase K (E. Mrrck) was added at a ratio of 20 μg proteinase K/50 μg protein. The solutions were incubated in a 37° C. water bath and aliquots were withdrawn at 30, 60, 90 and 120 minutes. The aliquots were coated onto 96-well plates overnight at 4° C., fixed with 95 percent ethanol and the remaining sites on the plate blocked with 1 percent by weight BSA. The antigens were assayed by ELISA as described above, using LP3-IIG2 as the first step antibody.

Treatment with proteinase K substantially reduced the reactivity of the serogroup-common antigen with LP3-II2, indicating that the antigen is proteinaceous.

H. Purification and Labeling of LP3-IIG2

LP3-IIG2 antibody wa purified from ascites fluid prior to conjugation to fluorescein isothiocyanate (FITC, isomer II; Molecular Probes). Ascites fluid (3 ml) was loaded onto a protein A-Sepharose ® CL-4B column (Pharmacia Fine Chemicals; Sweden) equilibrated with 0.14 M sodium phosphate/1M NaCl/0.01 percent by weight sodium azide, pH 8.0 buffer. The column was washed with 0.1 M citrate/1M NaCl/0.01 percent azide, pH 6.0 buffer. Antibody waseeluted from the column with 0.1 M citrate/1M NaCl/0.01 percent azide pH 3.0 buffer. Fractions containing antibody weee combined and dialyzed against 0.29 M $CO_3$/1M NaCl/pH 9.3 buffer overnight at 4° C. One milligram aliquots of purified antibody were then labelled with either 20 or 40 μg of fluorescein isothiocyanate by incubation at 37° C. for 1 hour. Unconjugated fluorochrome was removed by passage through a Sephadex ® G-25 column equilibrated with 0.01 M $NaHCO_3$/ 1 M NaCl/0.1 mg/ml BSA/0.01 percent sodium azide, pH 9.3. The conjugated antibody was diluted 1:10 in PBS/ 1 mg/ml BSA/0.01 percent sodium azide with Evan's Blue (OD 620=0.9).

Antigen slides were prepared by suspending *L. pneumophila* microorganisms, serogroups 1–8, in 1% formalin in water to a concentration equivalent to 0.5 McFarland standard units. This suspension was diluted 1:20 and added to 10-well microscope slides (Carlson Scientific Inc.) in 20 μl/well amounts. The slides were dried on a slide warmer at 37° C. for 20 minutes. The conjugated antibodies were diluted to 25 μg/ml protein in a solution of 1% Triton ® X-100/100 mM EDTA in PBS at pH 8.5. The antibodies were added to the wells in 20 μl amounts and incubated at room temperature for 30 minutes. The antibody solution was removed by aspiration and the slides were washed with deionized water.

FITC-labeled LP3 IIG2 stained serogroups 1 through 8 of *L. pneumophila*. It did not stai a variety of other common respiratory pathogens.

LP3-IIG2 was further analyzed using two-dimensional gel elcctrophoresis. Nonequilibrium pH gradient electrophoresis ((NEPHGE) O'Farrell et. al., Cell 12:1133–1142 (1977)) was carried out in the first dimension using a cylindrical gel composed of 9 M urea, 2 percent (v/v) NP-40 (Shell Chemical Co.), 5 percent (v/v) Ampholines (pH 3.5–10), 4 percent acrylamide and 0.11 percent bisacrylamide. A sample of immunoglobulin (20 μg) was diluted to 50 μl in lysis buffer (9.5 M urea, 2 percent by weight NP-40, 2 percent Ampholines and 5 percent 2-mercaptoethanol). Electrophoresis was performed at 450 V for 6 hours with the anode at the top of the gel.

The second dimension electrophoresis was performed in a 12.5 percent acrylamide slab gel, with a 5 percent acrylaide stacking gel. The first dimension gel was equilibrated in 2X sample buffer (0.125 M tris pH 6.8, 2 percent SDS, 2 percent 2-mercaptoethanol and 0.1 percent bromophenol blue). Electrophoresis was performed at 60 V (constant voltage) until the bromophenol blue reached the bottom of the gel.

Following electrophoresis in the second dimension, the gel was stained with coomassie brilliant blue R250 (0.25 percent by weight CBBR in 40 percent methanol an 7.5 percent acetic acid) for 30 minutes and destained in 40 percent methanol and 10 percent acetic acid.

The antibody LP3 IIG2 contained one heavy chain, composed of multiple charge variants, and one light chain. The monoclonal origin of the immunoglobulin was thus verified.

Although the foregoing invention has been described in some detail by way of illustration and example for purposes of clarity of understanding, it will be obvious that certain changes and modifications may be practiced within the scope of the appended claims.

We claim:

1. A method for the detection and diagnosis of the bacterium *Legionella pneumophila* in biological specimens, said method comprising reacting a sample suspected of containing said bacterium with a labeled monoclonal antibody to a *Legionella pneumophila* proteinaceous serogroup-common antigen, wherein said antibody does not react with antigens of other Legionella species, and detecting the presence of a signal provided by said label.

2. The method of claim 1 wherein the serogroup-common antigen is a protein of molecular weight 28,000 to 29,000 Daltons and is capable of recognizing and specifically binding to monoclonal antibody LP3-IIG2 (ATCC HB 8472).

3. The method of claim 1 wherein the label is selected from the group consisting of fluorophores, enzymes, luminescent compounds, radioisotopes and particles.

4. The method of claim 3 wherein the label is a fluorophore.

5. The method of claim 4, wherein said sample is added to a solubilizing reagent either before or simultaneously with reacting said sample and the labeled antibody.

6. The method of claim 4 wherein the fluorophore is fluorescein isothcocyanate.

7. The method of claim 4, further comprising contacting said sample with a solubilizing reagent.

8. The method of claim 7, wherein said solubilizing reagent is selected from the group consisting of detergents, chelating agents and mixtures thereof.

9. The method of claim 7 further comprising immobilizing said sample on a solid substrate before contacting said sample with a solubilizing reagent.

10. Monoclonal antibodies which react with an antigenic determinant on an antigen common to at least serogroups 1 through 8 of *Legionella pneumophila and which determinant is not present in Pseudomonas fluorescens, Legionella bozemanii, Legionella micdadei, Legionella dumoffii, Legionella longbeachae* 1 and 2, *Legionella jordanis, Legionella Gourmanii, Legionella oakridgensis,* or *Legionella sainthelinsi.*

11. Antibodies as recited in claim 10, which are mammalian monoclonal antibodies.

12. Antibodies as recited in claim 11, wherein said mammal is a mouse.

13. Antibodies as recited in claim 10, having a label which provides a detectable signal.

14. Antibodies as recited in claim 13, wherein said label is seeected from the group consisting of radioactive isotopes, fluorescent compounds, chemiluminescent compounds, enzymes, magnetic labels and particles.

15. Antibodies as recited in claim 14, wherein said label is a fluorescent molecule.

16. Antibodies as recited in claim 15, wherein said fluorescent label is fluorescein isothiocyanate.

17. Antibodies as recited in claim 14, wherein said label is an enzyme.

18. Monoclonal antibodies which are capable of specifically recognizing and bindigg to an antigen derived from *Legionella pneumophila,* said antigen characterirzed in that it:

a. is present in at least serogroups 1 through 8 of *Legionella pneumophila;* b. is not present in other legionella species;

c. has a molecular weight between 28,000 and 29,000; and d is proteinaceous.

19. Monoclonal antibodies as recited in claim 18, wherein said antibodies are mammalian antibodies.

20. Antibodies as recited in claim 19, wherein said mammal is a mouse.

21. Antibodies as recited in claim 18, which have a label providing a detectable signal.

22. Antibodies as recited in claim 21, wherein said label is selected from the group consisting of radioactive isotopes, flurrescent compounds, chemiluminescent compounds, enzymes, magnetic labels and particles.

23. Antibodies as recited in claim 22, wherein said label is a fluorescent compound.

24. Antibodies as recited in claim 23, wherein said fluorescent compound is fluorescein isothiocyanate.

25. Antibodies as recited in claim 22, wherein said label is an enzyme.

26. The hybrid cell line identified as LP3-IIG2 (ATCC-HB-8472).

27. Monoclonal antibodies produced by the cell line of claim 26.

28. An antigen isolated from *Legionella pneumophila,* which antigen:

a. is present in at least serotypes 1 through 8 of *Legionella pneumophila;* b. is not present in *Pseudomonas fluorescens, Legionella bozemanii* or *Legionella micdadei;* c. has a molecular weight between 28,000 and 29,000;

d. is susceptible to degradation by proteinase K.

29. Monochlonal antibodies reactive with an antigenic determinant which is capable of being recognized and specifically bound by monoclonal antibodies identified as LP3-IIG2 (ATCC HB 8472).

* * * * *